(12) United States Patent
Hauger et al.

(10) Patent No.: US 6,763,259 B1
(45) Date of Patent: Jul. 13, 2004

(54) SURGICAL SYSTEM SUPPORTED BY OPTICAL COHERENCE TOMOGRAPHY

(75) Inventors: Christoph Hauger, Aalen (DE); Joachim Luber, Essingen (DE); Michael Kaschke, Oberkochen (DE); Margit Krause-Bonte, Aalen (DE)

(73) Assignee: Carl-Zeiss-Stiftung (DE), Heidenheim (DE)

( * ) Notice: Subject to any disclaimer, the term of this patent is extended or adjusted under 35 U.S.C. 154(b) by 209 days.

(21) Appl. No.: 09/609,671

(22) Filed: Jul. 3, 2000

(30) Foreign Application Priority Data

Jul. 2, 1999 (DE) .......................................... 199 30 408

(51) Int. Cl.⁷ ................................................ A61B 6/00
(52) U.S. Cl. ........................ 600/427; 600/476; 356/450
(58) Field of Search ................................ 600/476, 473, 600/407; 356/450, 479, 497, 498, 345, 351, 349, 356, 354

(56) References Cited

U.S. PATENT DOCUMENTS

| 4,748,686 A | * | 5/1988 | Glomb ......................... 324/96 |
| 5,795,295 A | | 8/1998 | Hellmuth et al. |
| 5,892,583 A | * | 4/1999 | Li .............................. 356/450 |
| 6,111,645 A | * | 8/2000 | Tearney et al. ............. 356/484 |
| 6,490,475 B1 | * | 12/2002 | Seeley et al. ............... 600/426 |

FOREIGN PATENT DOCUMENTS

| DE | 198 37 152 A1 | 8/1998 | ........... A61B/19/00 |
| EP | 0 581 871 B1 | 4/1992 | ............ G01B/9/02 |

* cited by examiner

*Primary Examiner*—Shawna J. Shaw

(57) ABSTRACT

An OCT-supported surgical system includes an OCT module that includes a surface scanner, the position of which can be sensed by a position sensing unit, and an evaluation and display unit, which is connected to the OCT module and to the position sensing unit in order to be able to correlate a tissue-differentiated tomogram of a specimen sensed by the OCT module with preoperatively produced specimen data.

45 Claims, 6 Drawing Sheets

SURGICAL SYSTEM SUPPORTED BY OPTICAL COHERENCE TOMOGRAPHY

STATEMENT REGARDING FEDERALLY SPONSORED RESEARCH OR DEVELOPMENT

Not applicable.

CROSS-REFERENCES TO RELATED APPLICATIONS

Not applicable.

BACKGROUND OF THE INVENTION

Field of the Invention

The invention relates to a surgical system supported by optical coherence tomography (OCT) and a path length variator for an interferometer, which can be arranged in an OCT-supported surgical system.

DISCUSSION OF RELEVANT ART

An OCT-supported surgical system is known, for example from U.S. Pat. No. 5,795,295.

BRIEF DESCRIPTION OF THE DRAWINGS

The invention will be explained by means of preferred embodiments and with the aid of the accompanying drawings, in which.

DETAILED DESCRIPTION OF PREFERRED EMBODIMENTS

Figure 1:
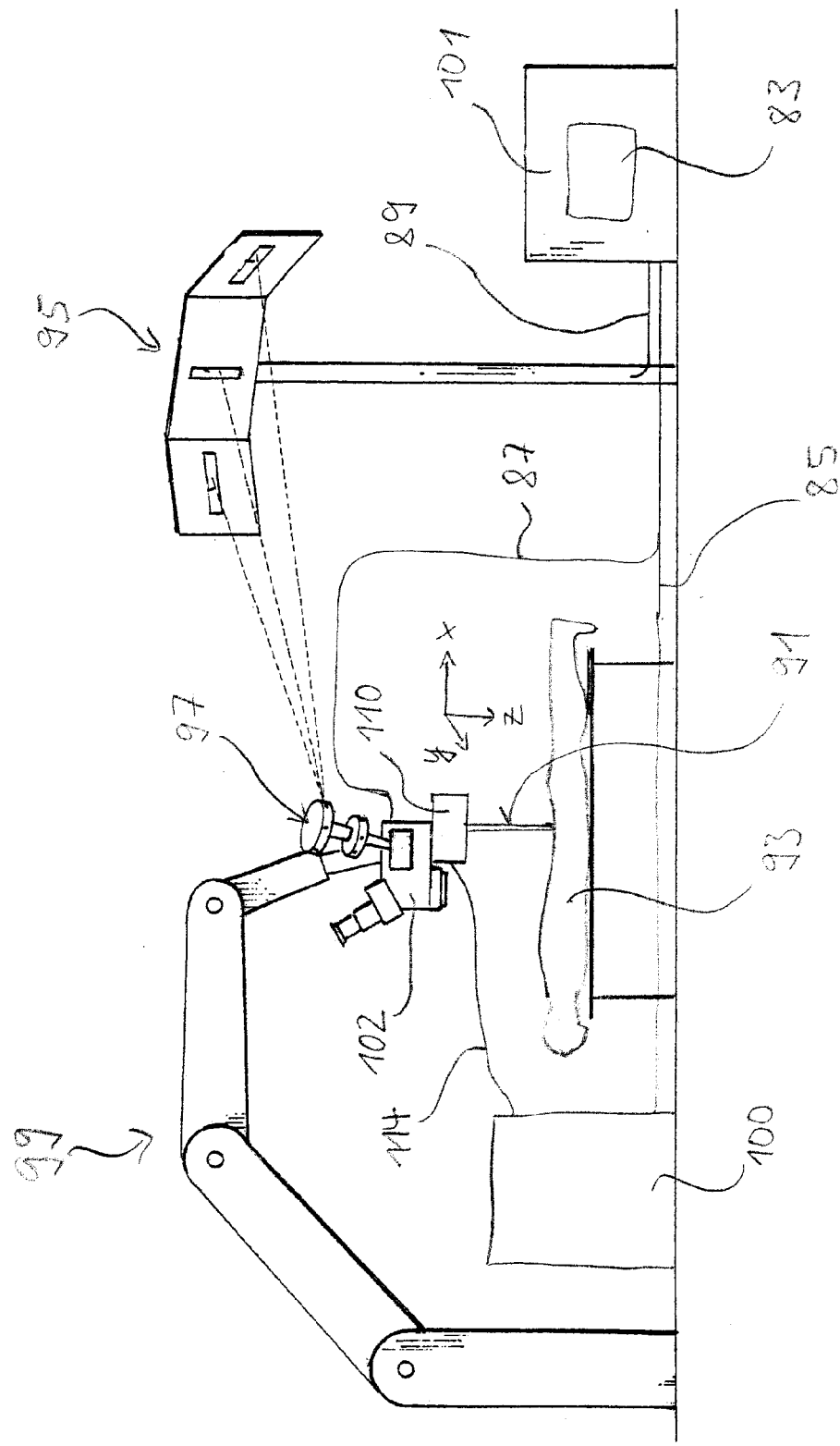
FIG. 1 shows an OCT-supported surgical system according to the invention, in schematic representation.
Figure 2:
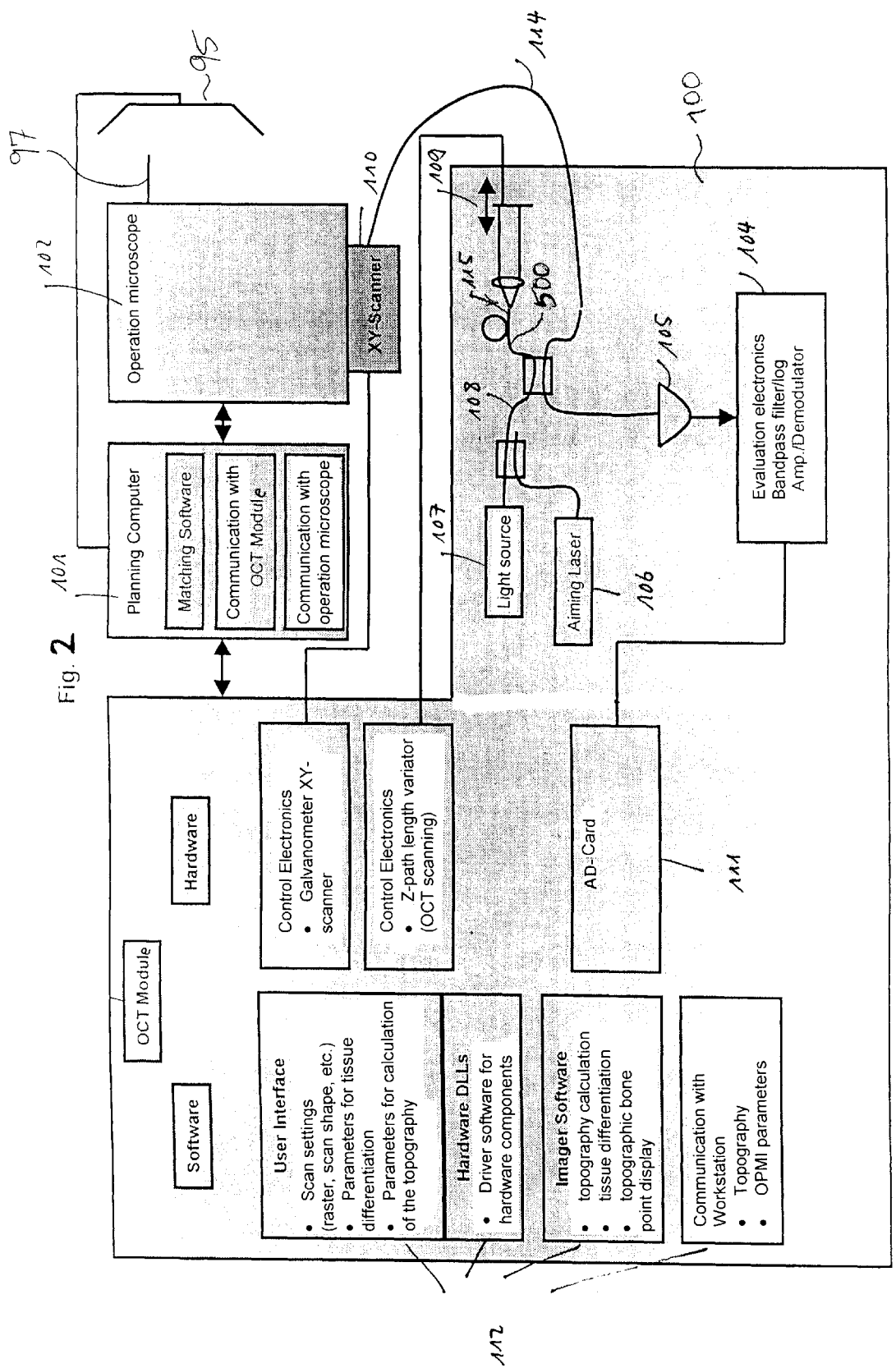
FIG. 2 shows a block diagram representation of the surgical system for navigation-supported vertebral column operation.

An OCT-supported surgical system according to the invention is schematically shown in FIGS. 1 and 2 as an example of a navigation-supported vertebral column operation.

An operation microscope 102 is displaceably and pivotably arranged on a jointed stand 99. The respective position and orientation of the operation microscope 102 at any given time is determined by a position sensing unit which includes sensing unit components 97 and 95. Such a position determination unit is known, e.g. from DE 198 37 152 A1.

An OCT module 100 is connected by a lead 114 to an XY-scanner 110 arranged on the operation microscope 102. The XY-scanner or surface scanner 110 can displace an OCT beam in the X- and Y-direction corresponding to the cartesian coordinate system indicated in FIG. 1 and thereby sense the surface of a patient 93, e.g., the open operation wound, in the X- and Y-directions.

The lead 114 includes both a data lead and also at least one optical fiber via which there are transported to the XY-scanner OCT radiation pulses of short coherence length and, if necessary, the radiation of a target laser or aiming laser integrated into the OCT module 100. The XY scanner can thereby scan the patient 93 with an OCT beam 91 which is preferably situated in the infrared. Additionally, and collinearly with the OCT beam 91, the XY-scanner or surface scanner 110 can also emit a visible aiming laser beam toward the patient 93.

An evaluation and indicating unit 101 (also termed "planning computer 101" hereinbelow) is connected to the position sensing unit, the operation microscope 102, and the OCT module 101, via data leads 89, 87 and 85. The planning computer 101 can effect time-resolved determination of the position of the operation microscope 102 relative to the patient 93 by means of the linking of the information relating to patient topography provided by the OCT module 100 and the information provided by the position sensing unit about the position of the operation microscope 102 and hence of the surface scanner 110.

The planning computer 101 includes a display screen 83 on which, e.g., there can be displayed, in a preoperatively determined CT image of the patient, the instantaneous position of the operation microscope 102 or the instantaneous position of a surgical instrument which is detectable by the position sensing unit, relative to the instantaneous position of the patient 93. The planning computer 101 can make position and navigation information available to the surgeon, making it possible for him to operate rapidly, precisely and safely.

CT data of the patient's vertebral column are taken by CT (computer tomography) before the operation proper. These CT data are stored in the planning computer 101 in the form of two-dimensional and three-dimensional data sets. In particular, the surface coordinates of the bone structures are known.

The surgeon uses these CT data for the planning of the operation. Thus, for example, positions of screws for the reinforcement of the vertebral column can be directly drawn in the CT display. At the beginning of the surgical operation, the part of the vertebral column which is relevant for the operation is exposed by the surgeon. When this is concluded, the so-called referencing follows: the coordinate position of the patient 93 in the operating theater has to be transformed into the coordinate system of the CT data in the planning computer 101. The operation can only take place with navigation support when this association of the two coordinate systems is known. In this case, the instantaneous position of the surgical instrument can be blended into the CT data. Furthermore, the surgeon can be guided (→navigation) to a determined anatomical location.

In the present invention, the process of the optical coherence tomography (OCT) is used for automatic referencing in operations on the vertebral column. As described, for example, in EP 0 581 871 B1, sectional images of biological specimens can be measured (optical ultrasound) by means of optical coherence tomography. Furthermore, the OCT is also suitable as a distance sensor with an accuracy in the region of a few micrometers. In order to carry out the referencing by means of the OCT, the topography of the vertebra exposed by the surgeon is measured by means of the OCT module 100 and the surface scanner 110 mounted on the operation microscope. This is followed by a matching of the OCT topography to the CT topography in the planning computer.

Since the actual OCT interference signals contain the optical echo of tissue structures down to a depth of about 2–3 mm, the OCT is used in the present invention for tissue differentiation. Since the stored CT data contain bone structures, it is appropriate for the OCT topography to contain exclusively bone points. For this reason, after the measurement of the OCT topography, a tissue differentiation is carried out, in which the bone points are used exclusively for matching to the CT data, by means of suitable evaluation of the OCT interference signals. Summarizing, the OCT-supported surgical system is thus used, on the one hand, as a surface sensor, and on the other hand for tissue differentiation.

The individual system components are described in further detail hereinbelow.

As mentioned hereinabove, the planning computer 101 contains the CT patient data. This planning computer 101 communicates with the operation microscope 102 and with the OCT module 100. The computer 101 furthermore contains the matching software which carries out a matching of the measured coordinates of the OCT topography to the CT topography, i.e., which correlates the patient topography sensed by the OCT module 100 with the CT data and brings them into correspondence.

A surface scanner 110 is integrated into the operation microscope 102, and has suitable scanning devices for the deflection of the OCT measuring beam 91 in two directions X and Y, and also a suitable optics for the imaging of the measuring beam onto the specimen surface. The position of the operation microscope is sensed in a known manner by means of the position sensing unit 95, 97. The coordinates of the respective present scanning location on the specimen or on the patient 93 are thus known at all times to the panning computer 101.

The OCT module includes a Michelson interferometer 108, a short-coherence light source 107, an aiming laser 106 in order to make the instantaneous scanning location visible on the specimen, a device 109 for the path length changing of the reference branch 115, a photodiode 105 for the detection of the interference signal, and also a suitable evaluation electronics 104 for the processing of the interference signal. The specimen branch 114 includes the above-described surface scanner 110.

The detection of an interference signal takes place in a known manner: because of the short coherence length of the light source, an interference signal is only detected when the optical path lengths of the specimen branch 114 and reference branch 115 are equal. The measurement of the OCT topography takes place in the following manner. The length of the reference branch 115 is periodically varied with the path length variator 109, by means of which the patient 93 is scanned by the OCT beam 91 in the Z-direction. The path length variation is typically about 50 mm for a vertebral column operation, and is substantially given by the height variation between spinous process and lamina, left and right of a vertebra. The specimen is scanned in the X- and Y-directions by the surface scanner 110, synchronously with this Z-path length variation. Typical scanning fields are likewise about 50 mm for the X- and Y-directions, and thus measure in all a volume of about 50 mm×50 mm×50 mm. A half period of the path length variator 109 is designated hereinbelow as the A-scan. Each A-scan contains, on the one hand, the coordinates of the surface points (X, Y), and on the other hand each A-scan, because of the penetration of the measuring light into the specimen, contains information concerning the tissue type (Z-information). The Z-resolution is determined by the coherence length of the light source 107 and is typically about 10 μm for the available light sources. The analog interference signal of the evaluation electronics is converted into a digital signal by an A/D converter 111. The coordinates of the measured surface points are calculated. A tissue differentiation is carried out and the coordinates of the remaining bone surface points are returned to the planning computer 101.

The OCT module is divided into further software and hardware components in FIG. 2. The software 112 can be separated into the packages of User Interface, Hardware DLLs, Imager Software and also Communication with the planning computer. The individual functions are briefly described in FIG. 2.

Figure 3:
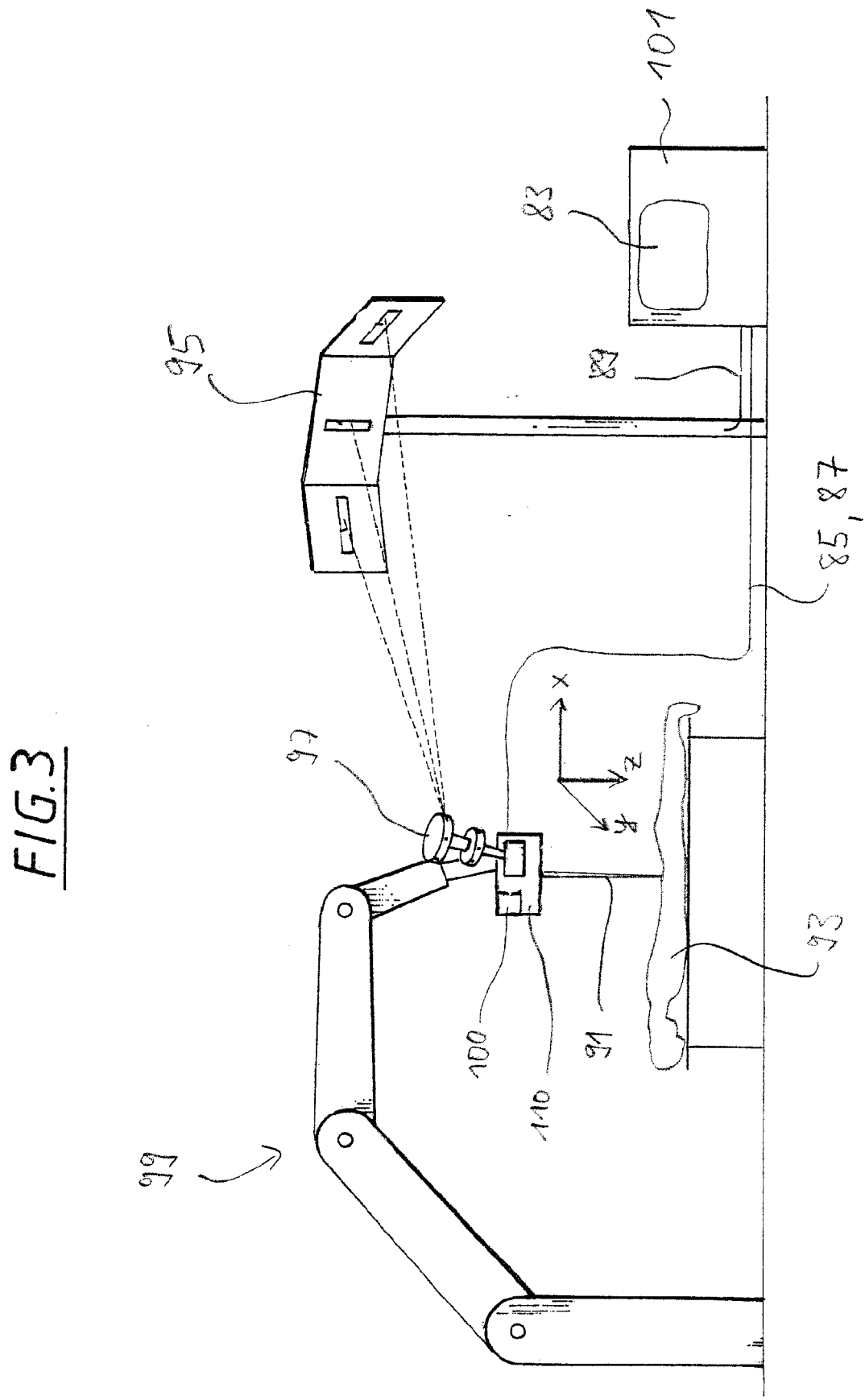
FIG. 3 shows a further embodiment of an OCT-supported surgical system, in a schematic representation.

FIG. 3 shows a further embodiment of an OCT-supported surgical system. In this case, differing from the OCT-supported surgical system of FIG. 1, no operation microscope 102 is used. The surface scanner 110 is arranged, together with the OCT module 100, directly on the stand 99, and carries the components 97 of the position sensing unit. Apart from this, the functions and also the course of the referencing proper are analogous to the surgical system of FIGS. 1 and 2.

The technical realization of referencing with the surgical system of FIGS. 1 and 2 will be described hereinbelow. The individual steps of the process of referencing are summarized in FIG. 4. The referencing process can be divided into three phases:

1. The production of the planning CT, 305; 2. Initial referencing 306 at the beginning of the operation; and
3. On-line referencing 307 during the operation.

1. Planning CT (305)

Figure 4:
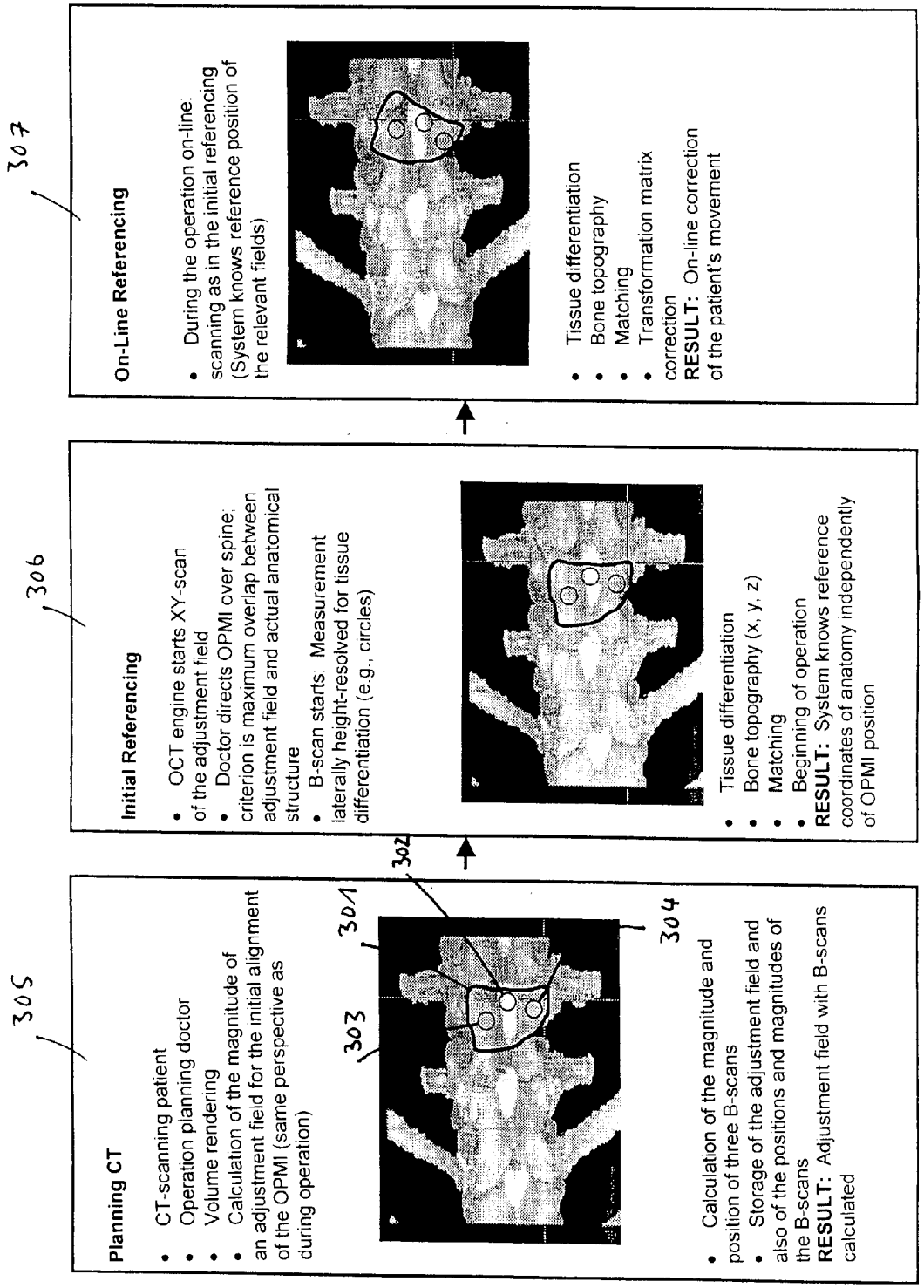
FIG. 4 shows a schematic representation of the course of the automatic referencing with an OCT-supported surgical system according to the invention.

A measurement of the patient's vertebral column takes place by means of CT in the first step, before the actual operation. The CT data are stored in the planning computer 101. The surgeon carries out the planning of the operation on this CT data set. It is thereafter known to the planning computer 101 which vertebra is to be operated on. In the next step, an adjustment field 301 is set. The adjustment field serves to limit the bone area relevant for referencing. The determination of the adjustment field can take place either automatically through the planning computer, or manually by the doctor. At least three scan lines 302, 303, 304 on the vertebra are then determined, and their surface coordinates are to be measured in the following OCT referencing. The setting of these scan lines can also take place either automatically by means of the software of the planning computer, or manually by the surgeon. Ideally, these three scan lines are situated on the spinous process and also on the right and left laminae of the vertebra to be referenced. Since each scan line consists of several OCT A-scans, the scan lines are hereinafter designated as B-scan lines. The B-scan lines are ideally constituted as circles, in order to cover as large as possible a region of the bone surface with as few as possible A-scans. The size and position of the B-scan lines are shown in FIG. 4. As a result of the planning CT phase, the size of the adjustment field and also the size and position of the B-scan lines are known to the planning computer 101.

2. Initial Referencing (306)

The initial referencing is carried out in the operating theater. The patient is in a state of general anesthesia, and is positioned on the operating table. The surgeon prepares and exposes the region of the vertebral column which is relevant for the operation. In particular, the spinous process and the right and left laminae are prepared. The surfaces of the exposed structures consist of varied tissue types. The surfaces of the right and left laminae and of the spinous process mainly consist of bone tissue, while fat, muscle, and connective tissue are present in the surrounding field. In the first step of the initial referencing, the surgeon starts the surface scanner 110. This first senses the contour of the adjustment field 301 stored in the planning computer 101. No OCT surface points are measured for this process; the surface scanner serves in this case only for visual marking of the contour of the adjustment field. The surgeon orientates the operation microscope 102 or the X-Y scanner 110 such that the adjustment field shows an optimum overlap with the patient's actual anatomical structure. By use of the aiming laser, the adjustment field is visible on the operation field as a stationary contour. After the conclusion of this coarse orientation, there takes place the actual measurement of the surface topography by means of OCT. The surface scanner 110 measures the B-scan lines stored in the planning computer. It is decisive for the subsequent tissue differentiation that these B-scan lines are sufficiently closely scanned, so that a correlation exists between neighboring surface points as regards the kind of tissue. If neighboring surface points are situated far apart from each other, no reliable statement can be made from a single A-scan concerning the kind of tissue. A sufficiently close sensing of the B-scan lines lies at a distance of about 200 μm between neighboring points. This gives a circle diameter of about 6 mm for a total of a hundred points per circular B-scan line. This value is a realistic magnitude for the anatomical circumstances. After measurement of the three B-scan lines, the coordinates of the surface points situated on them are then measured.

Figure 5:
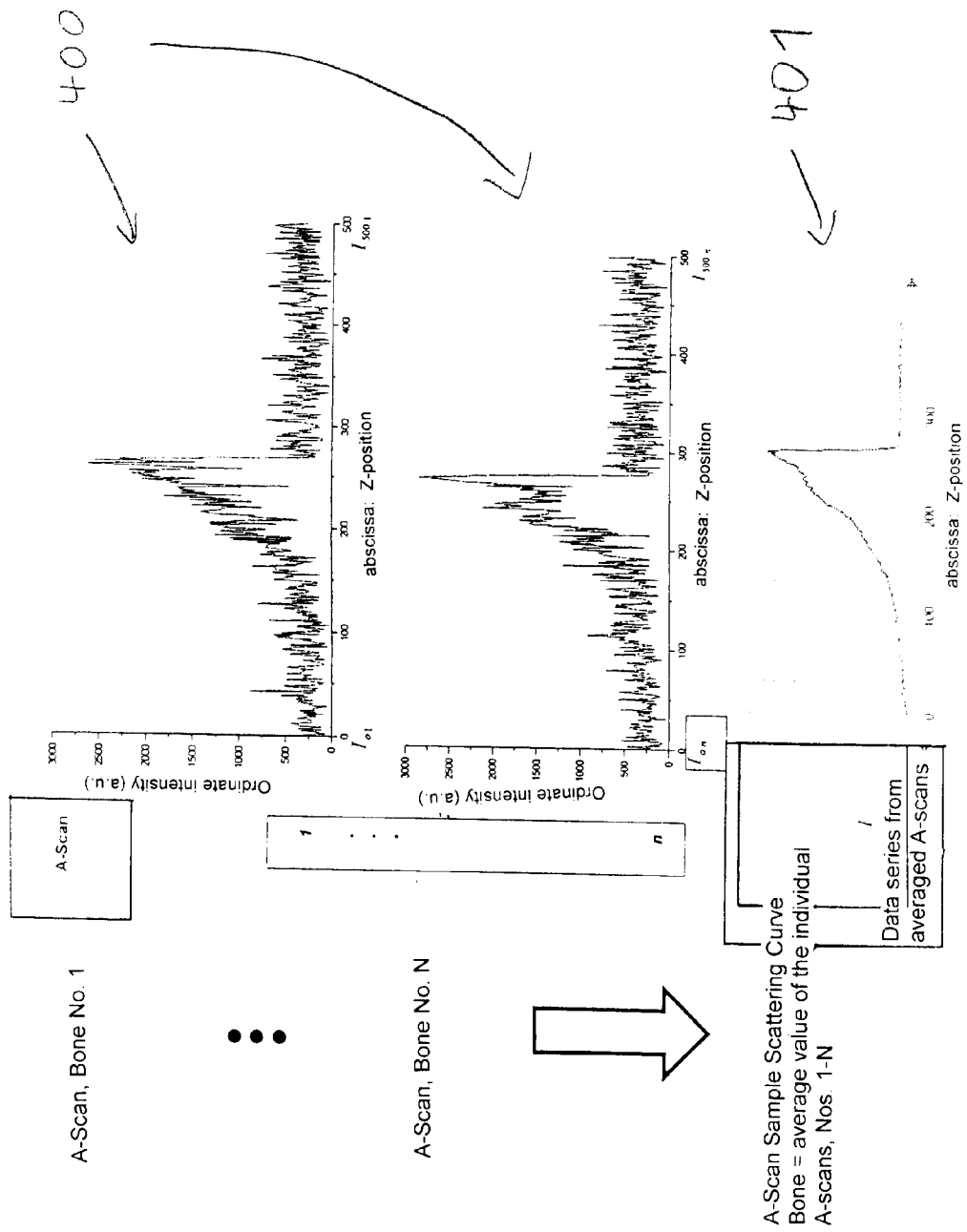
FIG. 5 shows a schematic representation of the production of an A-scan sample scatter curve of bone tissue for application to tissue differentiation with an OCT-supported surgical system according to the invention.

Tissue differentiation is carried out in the next step. The tissue differentiation is based on the evaluation of the Z-depth information of the individual A-scan lines of the B-scan lines 302, 303, 304. The course of the A-scan lines is determined by the scattering and absorption properties of the different kinds of tissue and represents the optical echo of these tissue structures. In order to carry out a tissue differentiation, an A-scan sample scattering curve is first determined in in vivo trials, as shown in FIG. 5. A sample scattering curve 401 is generated by forming an average of measurements of very many A-scans 400 of bones of different vertebrae. The generation of this A-scan sample scattering curve for bones has to take place in a one-time measurement series evaluation, before use of the surgical system. During the initial referencing, and later also in on-line referencing, all the detected A-scans of the B-scan lines are compared with this sample scattering curve, with the aid of a suitable software algorithm. Formation of the cross-correlation represents a possibility for comparison. The value thus obtained is a measure of the agreement between the present A-scan and the bone sample scattering curve. An experimentally determined boundary value is available as the criterion according to which the bone tissue points can be distinguished from points from other tissues. As mentioned above, this simple evaluation of individual A-scans is not sufficient to ensure a reliable tissue differentiation, since chance tissue structures can give a false positive result. For this reason, the close sensing of B-lines is effected in the present invention, as described hereinabove. With this method of proceeding, neighboring A-scans can be compared by the use of known image processing algorithms, and are thus brought into play as additional criteria for a reliable tissue differentiation.

After the conclusion of the tissue differentiation, the coordinates (X, Y, Z) of the bone surface points are available in the OCT module 100. These coordinates are transmitted to the planning computer. Matching of the OCT coordinates with the CT coordinates takes place there. The position of the patient in the operating theater is now known. The operation can begin under navigation support.

3. On-Line Referencing (307)

A change in the position of the patient determined in the initial referencing mainly occurs due to the patient's respiration and to displacements of the vertebrae due to the surgical intervention. Considerable danger to the patient exists because of lack of knowledge of the exact patient position during the operation. It is therefore very important for the precision of the operation to sense movements of the patient on-line during the operation and to correct on-line for such movements. For this reason, the three B-scan lines of the initial referencing are measured on-line by means of the surface scanner 110. Based on the initial referencing, the coordinates of the surface points of these three scan lines are known to the surgical system. If a change of position of the patient's position now occurs, changed coordinates are measured for the surface points of the B-scan lines. These changed coordinates are measured on-line and are evaluated in the OCT module. A tissue differentiation is carried out, analogously to the initial referencing. The matching of the changed surface coordinates takes place on the planning computer 101, analogously to the initial referencing. An on-line correction of the present patient position is thereby obtained. The position of the patient is thus known at all times during the operation.

Figure 6:
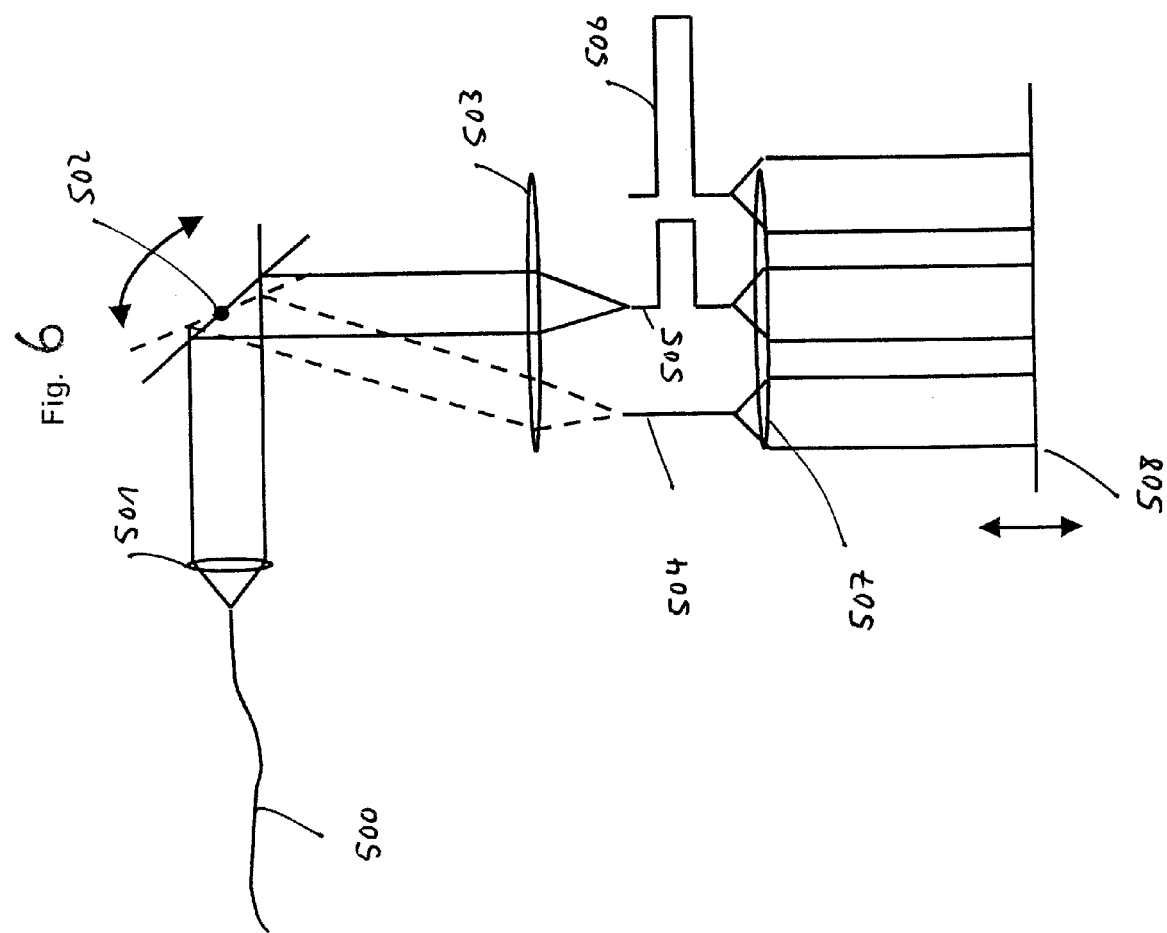
FIG. 6 shows a path length variator for the reference arm of a Michelson interferometer contained by a surgical system according to the invention, permitting a short referencing measurement time.

Path Length Variator for Increasing the Measurement Speed (FIG. 6) of Referencing The measurement speed of the surgical system is determined by the path length variator 109. The frequency with which the whole Z-path length difference is passed through determines the frequency with which the surface points are measured. The aim is an on-line referencing during the operation. A measurement of the surface topography is to be concluded in one second during the on-line referencing. In this time, the three B-scan lines 302, 303, 304 have to be measured. As mentioned hereinabove, a sufficiently close sensing of the surface points has to take place for the tissue differentiation. Supposing that there are a hundred surface points per scan line, three hundred surface points have to be measured in a second. The frequency of the path length variator should therefore be 300 Hz or more. Typical Z-height differences between the spinous process and the lamina of a vertebra are about 30–50 mm. The path length variator must consequently sweep over a stroke in the Z-direction of at least 50 mm, in order to be able to measure all the relevant structures. The difficulty in reducing the measurement time consists of passing through a large Z-stroke (50 mm) in a short time. After the conclusion of the initial referencing, however, the actually occurring Z-coordinates of the vertebra are known, so that by the use of this information, the whole of the depth region no longer has to be measured. This information about the actually existing Z-coordinates is used in the path length variator according to FIG. 6, in order thus to reduce the measurement time. The light emitted from the fiber 500 of the reference branch 115 is collimated by a lens 501 and passed to a pivotable scanning mirror 502. This scanner 502 deflects the light and couples it according to the pivoting position into one of three different fiber optic delay lines 504, 505, 506. The coupling into the fiber optic delay lines takes place by focusing by means of a lens 503. The optical path length of the fiber optic delay lines increases from 504 through 506. After passing through the respective fiber optic delay line, a collimation of the light is effected by the lens 507. The collimated beam is incident on a periodically moved mirror 508. If now the initial referencing is carried out with this path length variator of FIG. 6, it is then (as mentioned hereinabove) necessary to measure a depth region of about 50 mm. The periodically moved mirror 508 is periodically moved, in the case shown in FIG. 6, with a depth stroke of about 17 mm. Synchronously with this movement, the scanner 502 couples light in a successive time sequence into the three fiber optic delay lines 504–506. The increase of the optical path length at any given time is just 17 mm, so that with the arrangement shown the desired Z-path length change of 3*17 mm=51 mm can be attained. Since the periodically moved mirror 508 has to sweep in this case over a stroke of only about 17 mm, this mirror can be moved considerably more quickly in comparison with a stroke of the whole 50 mm. In particular, the surface coordinates of the B-scan lines of the vertebra are known after the initial referencing. If these surface coordinates are situated in a Z-depth region which can be sensed, for example, by only two of the three optical delay lines (e.g., by 504 and 506), the light can be coupled exclusively into the delay lines 504 and 506 during the on-line referencing by means of the scanner 502, which further shortens the effective measurement time for the on-line referencing. In the path length variator shown in FIG. 6, three delay lines are illustrated. An increase of the number of the delay lines is possible and reinforces the described effect of measurement time shortening.

We claim:

1. A OCT-supported surgical system, comprising:
   an OCT module which includes a surface scanner,
   a position sensing unit that senses the position of said surface scanner, and
   an evaluation and display unit connected to said OCT module and to said position sensing unit, whereby a tomogram of a specimen comprising bones which is sensed by said OCT module is correlated with specimen data produced preoperatively, whereby said evaluation and display unit stores preoperatively produced specimen data most sensitive to a particular tissue,
   whereby said OCT module produces a tissue differentiated tomogram of said specimen which shows the coordinates of the bone surface points,
   and which contains topographic information exclusively of said particular tissue, and
   whereby said evaluation and display unit references said preoperatively produced specimen data according to said tissue differentiated tomogram.

2. The OCT-supported surgical system according to claim 1, wherein said OCT module includes a referencing module.

3. The OCT-supported surgical system according to claim 1, wherein said evaluation and display unit includes an adjustment field setting module.

4. The OCT-supported surgical system according to claim 1, wherein said evaluation and display unit includes a scan line setting module.

5. The OCT-supported surgical system according to claim 4, wherein said scan line setting module sets at least one scan line that is closed.

6. The OCT-supported surgical system according to claim 5, wherein said scan line setting module sets a plurality of mutually spaced-apart scan lines that are closed.

7. The OCT-supported surgical system according to claim 5, wherein said scan line setting module sets a circular scan line.

8. The OCT-supported surgical system according to claim 1, wherein said OCT module includes an adjustment field sensing module that controls said surface scanner.

9. The OCT-supported surgical system according to claim 1, wherein said OCT module includes an aiming laser.

10. The OCT-supported surgical system according to claim 9, wherein said aiming laser is constituted for intraoperative representation of contours on a patient.

11. The OCT-supported surgical system according to claim 1, further comprising a operation microscope that carries said surface scanner.

12. The OCT-supported surgical system according to claim 11, wherein said operation microscope is arranged on a hand-guided stand.

13. The OCT-supported surgical system according to claim 1, further comprising a stand that directly carries said surface scanner.

14. The OCT-supported surgical system according to claim 13, wherein said stand comprises a hand-guided stand.

15. The OCT-supported surgical system according to claim 13, wherein said stand is displaceable by a motor.

16. The OCT-supported surgical system according to claim 1, wherein said OCT module includes a Michelson interferometer with a path length variator that has a plurality of fiber optic delay lines.

17. The OCT-supported surgical system according to claim 16, wherein said path length variator includes a pivotable scanning mirror for coupling radiation into said plurality of fiber optic delay lines.

18. The OCT-supported surgical system according to claim 17, further comprising a displaceable reflector arranged at the side of said fiber optic delay lines that is remote from said scanning mirror.

19. The OCT supported surgical system according to claim 1, wherein said tissue differentiated tomogram is generated by comparing a depth dependence of signals generated by said OCT module with a stored sample scattering curve recorded in a one-time measurement series evaluation.

20. A path length variator associated with a Michelson interferometer, comprising a plurality of fiber optic delay lines and a pivotable scanning mirror for coupling radiation into said plurality of fiber optic delay lines, said plurality of fiber optic delay lines guiding light to a mirror which is periodically moved synchronously with said pivotable scanning mirror.

21. The path length variator according to claim 20, comprising a displaceable reflector arranged at the side of said fiber optic delay lines that is remote from said scanning mirror.

22. A OCT-supported surgical system, comprising:
   an OCT module which includes a surface scanner,
   a position sensing unit that senses the position of said surface scanner, and
   an evaluation and display unit connected to said OCT module and to said position sensing unit,
      whereby a tomogram of a specimen sensed by said OCT module is correlated with specimen data produced preoperatively,
      wherein said OCT module produces a tissue-differentiated tomogram of said specimen,
      said OCT module includes a referencing module,
      said evaluation and display unit includes an adjustment field setting module,
      said evaluation and display unit includes a scan line setting module,
      said scan line setting module sets at least one scan line that is closed, and
      said scan line setting module sets a plurality of mutually spaced-apart scan lines that are closed, and whereby said OCT module produces a tissue differentiated tomogram which shows the coordinates of the bone surface points.

23. A OCT-supported surgical system, comprising:
an OCT module which includes a surface scanner,
a position sensing unit that senses the position of said surface scanner,
a microinterferometer with a path length variator comprising a plurality of fiber optic delay lines, and
an evaluation and display unit connected to said OCT module and to said position sensing unit, whereby a tomogram of a specimen sensed by said OCT module is correlated with specimen data produced preoperatively, whereby said evaluation and display unit stores preoperatively produced specimen data most sensitive to a particular tissue,
whereby said OCT module produces a tissue differentiated tomogram of said specimen containing topographic information exclusively of said particular tissue, and whereby said evaluation and display unit references said preoperatively produced specimen data according to said tissue differentiated tomogram,
and whereby said OCT module produces a tissue differentiated tomogram which shows the coordinates of the bone surface points.

24. The OCT-supported surgical system according to claim 23, wherein said OCT module produces a tissue-differentiated tomogram of said specimen.

25. The OCT-supported surgical system according to claim 23, wherein said OCT module includes a referencing module.

26. The OCT-supported surgical system according to claim 23, wherein said evaluation and display unit includes an adjustment field setting module.

27. The OCT-supported surgical system according to claim 23, wherein said evaluation and display unit includes a scan line setting module.

28. The OCT-supported surgical system according to claim 27, wherein said scan line setting module sets at least one scan line that is closed.

29. The OCT-supported surgical system according to claim 28, wherein said scan line setting module sets a plurality of mutually spaced-apart scan lines that are closed.

30. The OCT-supported surgical system according to claim 28, wherein said scan line setting module sets a circular scan line.

31. The OCT-supported surgical system according to claim 23, wherein said OCT module includes an adjustment field sensing module that controls said surface scanner.

32. The OCT-supported surgical system according to claim 23, wherein said OCT module includes an aiming laser.

33. The OCT-supported surgical system according to claim 32, wherein said aiming laser is constituted for intra-operative representation of contours on a patient.

34. The OCT-supported surgical system according to claim 25, further comprising a operation microscope that carries said surface scanner.

35. The OCT-supported surgical system according to claim 34, wherein said operation microscope is arranged on a hand-guided stand.

36. The OCT-supported surgical system according to claim 23, further comprising a stand that directly carries said surface scanner.

37. The OCT-supported surgical system according to claim 36, wherein said stand comprises a hand-guided stand.

38. The OCT-supported surgical system according to claim 36, wherein said stand is displaceable by a motor.

39. The OCT-supported surgical system according to claim 23, comprising a Michelson interferometer associated with said path length variator.

40. The OCT-supported surgical system according to claim 39, wherein said path length variator includes a pivotable scanning mirror for coupling radiation into said plurality of fiber optic delay lines.

41. The OCT-supported surgical system according to claim 40, further comprising a displaceable reflector arranged at the side of said fiber optic delay lines that is remote from said scanning mirror.

42. The OCT-supported surgical instrument according to claim 23, wherein the path length variator is associated with a Michelson interferometer and a pivotable scanning mirror for coupling radiation into said plurality of fiber optic delay lines.

43. The path length variator according to claim 42, comprising a displaceable reflector arranged at the side of said fiber optic delay lines that is remote from said scanning mirror.

44. The OCT supported surgical system according to claim 23, wherein said tissue differentiated tomogram is generated by comparing a depth dependence of signals generated by said OCT module with a stored sample scattering curve recorded in a one-time measurement series evaluation.

45. A OCT-supported surgical system, comprising:
an OCT module which includes a surface scanner,
a position sensing unit that senses the position of said surface scanner, and
an evaluation and display unit connected to said OCT module and to said position sensing unit,
whereby a tomogram of a specimen sensed by said OCT module is correlated with specimen data produced preoperatively,
wherein said OCT module produces a tissue-differentiated tomogram of said specimen,
said OCT module includes a referencing module,
said evaluation and display unit includes an adjustment field setting module,
said evaluation and display unit includes a scan line setting module,
said scan line setting module sets at least one scan line that is closed, and
said scan line setting module sets a plurality of mutually spaced-apart scan lines that are closed.

* * * * *